United States Patent [19]

Kuper

[11] 4,038,326

[45] July 26, 1977

[54] UNSATURATED ALICYCLIC CARBINOLS AND DICARBINOLS AND METHOD OF PREPARATION

[75] Inventor: Donald G. Kuper, Bartlesville, Okla.

[73] Assignee: Phillips Petroleum Company, Bartlesville, Okla.

[21] Appl. No.: 629,431

[22] Filed: Nov. 6, 1975

Related U.S. Application Data

[63] Continuation of Ser. No. 344,468, March 23, 1973, abandoned.

[51] Int. Cl.$^2$ .............................................. C07C 33/05
[52] U.S. Cl. ........................... 260/617 C; 260/468 M; 260/514 M; 260/598; 260/610 R; 260/610 B; 260/617 HF; 526/72
[58] Field of Search ........ 260/610 R, 610 B, 617 HF, 260/632 HF, 468 M, 514 M, 598, 617 C

[56] References Cited

U.S. PATENT DOCUMENTS

| | | | |
|---|---|---|---|
| 2,619,506 | 11/1952 | Bardenca | 260/617 HT |
| 2,738,730 | 3/1956 | Staib et al. | 260/617 HF |
| 2,810,748 | 10/1957 | Stewart et al. | 260/617 HF |
| 3,023,249 | 2/1962 | Hutchinson | 260/610 B |

*Primary Examiner*—Norman Morgenstern

[57] ABSTRACT

An unsaturated alicyclic carbinol or dicarbinol, e.g., 4-cyclohexene methanol or 4-cyclohexene-1,2-dimethanol, is obtained by subjecting a diolefin oxidation product, i.e., a polymeric peroxide, e.g., 1,3-butadiene polyperoxide, to Oxo reaction conditions, including an elevated temperature of the order of about 100° to about 200° C and carbon monoxide and hydrogen under elevated pressure in presence of a metal carbonyl catalyst, subjecting reaction mixture thus obtained to known hydrogenation or reducing conditions to convert carbonylic groups to hydroxyl groups employing a catalyst and hydrogen or a reducing agent, e.g., LiAlH$_4$, the conditions being selective to preserve the unsaturated linkage desired in the product.

43 Claims, No Drawings

UNSATURATED ALICYCLIC CARBINOLS AND DICARBINOLS AND METHOD OF PREPARATION

This application is a continuation of application Ser. No. 344,468, filed Mar. 23, 1973, now abandoned.

This invention relates to the conversion of conjugated diolefin oxidation products to unsaturated alicyclic carbinols and dicarbinols.

In one of its concepts, the invention provides a process which comprises applying to a conjugated diolefin oxidation product reaction mass a combination of an Oxo reaction operation and a hydrogenation or reducing operation, to produce an unsaturated alicyclic carbinol or dicarbinol.

In another of its concepts, the invention provides a process which produces a compound having a structure which can be represented by the following:

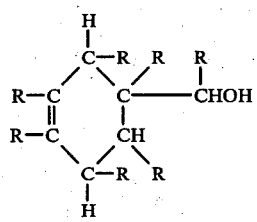

I in which R can be hydrogen or methyl and no more than 3 R's can be methyl,

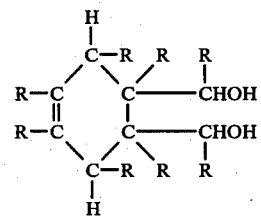

II in which R can be hydrogen or methyl, and in which no more than 4 R's can be methyl.

I have now conceived a process for the product of a carbinol or dicarbinol from an unsaturated hydrocarbon by subjecting a diolefin oxidation reaction product, that is, a polymeric peroxide, for example, as described in U.S. Pat. No. 3,023,249, issued Feb. 27, 1962, William M. Hutchinson, to Oxo reaction conditions including an elevated temperature of the order of about 100°–200° C and a pressure of carbon monoxide and hydrogen in the presence of a metal carbonyl catalyst to obtain a reaction mixture and then subjecting the mixture thus obtained to hydrogenation conditions in the presence of a catalyst such as a modified platinum catalyst and hydrogen and/or to reducing conditions by using a reducing agent, e.g., lithium aluminum hydride.

An object of the invention is to produce a carbinol or dicarbinol. Another object of the invention is to convert a conjugated diolefin oxidation product to produce an unsaturated alicyclic carbinol and/or dicarbinol. A further object of the invention is to provide a combination of steps for converting a polymeric peroxide to a carbinol and/or dicarbinol by a series of steps which do not require separation of intermediate products which may be obtained during practice of such steps.

Other aspects, concepts, objects and the several advantages of the invention are apparent from a study of this disclosure and the appended claims.

According to the present invention, there is provided a process for producing unsaturated alicyclic carbinols and/or dicarbinols by subjecting a diolefin oxidation product, i.e., a polymeric peroxide, to an elevated temperature of the order of about 100° to about 200° C in the presence of a pressure of carbon monoxide and hydrogen in the presence of a metal carbonyl catalyst to produce a reaction mixture in which the peroxidic material has been appreciably consumed and then subjecting the reaction mixture thus obtained to reducing conditions.

The reducing conditions can be applied as with a modified hydrogenation catalyst and hydrogen under hydrogenation conditions or as by using a reducing agent, e.g., lithium aluminum hydride.

According to the invention, the conditions are selected to preserve the unsaturated linkage desired in the product. Thus, the conditions of temperature and catalyst and related conditions are selected to avoid saturation of the unsaturated linkage desired in the product.

The polymeric oxidation product which is used as starting material of the invention is one which is obtained by oxidation of a conjugated diolefin starting material selected from the group of diolefins having the formula

wherein R is selected from the group consisting of a hydrogen atom and a methyl radical, and at least two of said R substituents are hydrogen, said oxidation product comprising repeating units of the type $\{R'-O-O\}$ wherein R' is selected from the group consisting of

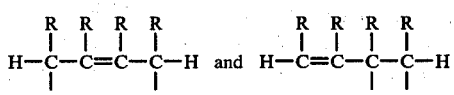

wherein R is as defined above. The process comprises forming said polymeric oxidation product by reacting said diolefin and oxygen at a temperature within the approximate range of 71° to 150° C, said reaction being carried out under a partial pressure of oxygen of at least 20 pounds per square inch sufficient to maintain said conjugated diolefin starting material in liquid phase and for a period of time within the range of 0.1 to 25 hours.

Starting materials applicable to the process are the conjugated diolefins of the formula:

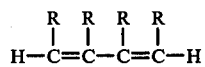

wherein the R's can be hydrogen or methyl groups and at least two of the R's are hydrogen. Typical conjugated diolefins applicable to the present invention include 1,3-butadiene, isoprene (2-methyl-1,3-butadiene), piperylene (1,3-pentadiene), 2,3-dimethyl-1,3-butadiene, and the like.

The above diolefins can be converted by a suitable oxidation process wherein a substantial portion of diolefin is converted to peroxidic polymer by liquid phase oxidation of a candidate conjugated diolefin with air or oxygen. When operating by the method the conjugated diolefin oxidation reaction can be conducted in any suitable pressure reactor provided with means to thoroughly mix air or oxygen and diolefin. Contact times in the oxidation step will be from 0.1 to 25, preferably 1 to 5 hours in duration. Said oxidation step is conducted within the temperature range of 50° C to 150° C and at a partial pressure of oxygen above 20 pounds per square inch and generally not over 4000 pounds per square inch. Preferred operation will be in the range from 100 to 400 pounds per square inch. The total pressure of the system will be sufficient to maintain a conjugated diolefin liquid phase. It is usually preferred to employ an initiator to start the oxidation reaction. Suitable materials which can be used for this purpose include peroxides or hydroperoxides, diazothioethers, and others known in the art. Oxidation promoters such as acetaldehyde, cobalt linoleate, and the like are also employed in the oxidation reaction. The oxidation effluent will comprise polymeric peroxidic materials containing repeating units of the types $$(-\overset{|}{C}-\overset{|}{C}=\overset{|}{C}-\overset{|}{C}-O-O-) \quad (1)$$

$$\begin{array}{c}(-\overset{|}{C}-\overset{|}{C}-O-O-)\\ |\\ -C=C-\\ |\end{array} \quad (2)$$

which are referred to as diolefin peroxides, together with carbonylic compounds having the same carbon skeleton as the diolefin starting material or multiples thereof.

The disclosure of U.S. Pat. No. 3,023,249, above mentioned, is incorporated herein by reference.

As noted, the Oxo reaction of this invention involves the treatment of the polymeric peroxide as defined above with carbon monoxide (CO) and hydrogen ($H_2$) in the presence of a metal carbonyl catalyst.

Suitable metal carbonyl catalysts are those wherein the metal is selected from Group VIII of the Periodic Table and preferably from the group consisting of cobalt, rhodium and iridium. Examples of preferred metal carbonyls include $Co_2(CO)_8$, $Rh_2(CO)_8$, $Ir_2(CO)_8$ and the like. It is known that in the presence of $H_2$ and CO the metal carbonyls are transformed to hydrocarbonyl compounds, e.g., $HCo(CO)_4$. These compounds could possibly be the reactive components in the mixture. J. Am. Chem. Soc., 85, 2782–4 (1963) and earlier references cited therein.

The amount of metal carbonyl catalyst employed is generally within the range of from 1–10 parts by weight per 100 parts by weight of the polymeric peroxide.

The CO pressure employed can be about 1000 psig but higher or lower pressures can be employed if desired. Likewise, the $H_2$ pressure employed will be about 1000 psig with higher or lower pressures also being suitable.

The temperature employed for the reaction of the polymeric peroxide with CO and $H_2$ in the presence of the metal carbonyl catalyst in this invention is generally within the range of about 100° C to about 200° C.

The time employed for the reaction described above is from about 1 hour to about 8 hours.

One skilled in the art in possession of this disclosure having studied the same can determine by mere routine test conditions outside those given herein at which he may desirably operate. The conditions now given are those which are presently preferred as encompassing the best mode of operation of the invention.

According to this invention, the reaction mixture obtained by subjecting the polymeric peroxide to Oxo reaction conditions is next subjected to hydrogenation reaction conditions. These conditions are believed to reduce any carbonylic groups present in the reaction mixture to hydroxyl groups, e.g.,

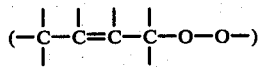

is converted to —$CH_2OH$. However, said hydrogenation is conducted under such selective conditions that any carbon-carbon double bonds present in the material being so treated are essentially unaffected. The manner of achieving the above selective hydrogenation is well known to those skilled in the art and includes the use of such reagents as $LiAlH_4$, $NaBH_4$, $LiBH_4$, and the like. Also suitable is a platinum catalyst, modified with, say, zinc and/or ferrous salts, and $H_2$. The conditions for use of the above reagents are known in the art and are employed to the extent that no substantial detectable carbonylic group remains in the reaction mixture.

In the performance of this selective hydrogenation step it is usually not necessary to remove the metal carbonyl catalyst or residue thereof remaining from the Oxo reaction step.

Product recovery from the selective hydrogenation step is by conventional means and the product can be further purified by conventional means such as fractional distillation and the like.

The products obtained from the above described sequence of reaction steps can be broadly described as unsaturated carbinols and unsaturated dicarbinols, and more particularly as cycloalkenylalkanols and bis(hydroxyalkyl)-cycloalkenes. For example, in the example below, the major products obtained when the polymeric peroxide of butadiene was used according to this invention were 4-cyclohexenylmethanol (A) and 4,5-bis(hydroxymethyl)cyclohexene (B) which can also be named as 4-cyclohexene-1,2-dimethanol.

The former compound (A) can be hydroformylated and then reduced to provide 1,4-bis(hydroxymethyl)cyclohexane, a valuable monomer in the preparation of polyesters. The compound (A) can also be subjected to oxidation to provide tricarboxylic acids useful as complexing agents or as a trifunctional monomer in polyester or polyamide synthesis. It can also be utilized as a solvent.

The latter compound (B) can be employed as a monomer in the synthesis of polyesters wherein the carbon-carbon double bond can serve as a reactive site for polymer modification to improve dyeability and the like. This compound can likewise be oxidized to produce a tetracarboxylic acid useful as a sequestering agent and the like.

EXAMPLE

1. Preparation of Polymeric Peroxide from 1,3-Butadiene

A reactor was charged with 6.0 grams of 1,3-butadiene and 50 ml benzene. The reactor was flushed with oxygen then pressured to 50 psig with oxygen at room temperature then heated to 85° C. During the course of about 16 hours reaction period the reactor was repressured twice to about 100 psig. At the end of the reaction period the reaction mixture was cooled to room temperature, vented and a 2-gram sample of the reaction mixture was titrated with 0.1N $Na_2S_2O_3$ to assay peroxide content. The sample required 26.1 ml of the titrant to reach the end point.

Another reactor charge was made employing 50 ml benzene and 11.0 g of 1,3-butadiene and the reaction carried out in the manner described above. A 2-gram sample of this reaction mixture required 23.9 ml of 0.1N $Na_2S_2O_3$ to reach the end point.

The two reaction mixtures were combined and diluted to 300 ml with benzene. A 2-gram sample of this mixture required 9.4 ml of 0.1N $Na_2S_2O_3$ to reach the end point.

2. Reaction of Polymeric Peroxide with $H_2$, CO and $Co_2(CO)_8$

The above mixture and 0.5 g $Co_2(CO)_8$ were charged to a 1-liter autoclave. The system was flushed with CO then pressured to 600 psig with CO. Hydrogen was next pressured into the reactor to provide a pressure of 1100 psig. The mixture was heated to 121° C and maintained at that temperature for 2 hours with stirring. The reactor was cooled, vented and opened. However, the odor of peroxidic material was detected so the reactor was closed and repressed to 1000 psig with CO and an additional 1000 psig with $H_2$. The mixture was heated at 121° C with stirring for 2.5 hours. The reactor was then cooled, vented and the mixture removed. A 2-gram sample of this mixture required 0.3 ml of 0.1N $Na_2S_2O_3$ to reach the end point. This mixture was then concentrated by vacuum evaporation of diluent and other volatile impurities and byproducts at room temperature.

3. Hydrogenation of Reaction Mixture from Oxo Reaction

The concentrate (7.6g) from step 2 above was dissolved in about 15 ml benzene then added dropwise to a suspension of 8.0 g $LiAlH_4$ in 300 ml ether with stirring. After the addition was complete the mixture was heated to reflux for about four hours. Excess $LiAlH_4$ was destroyed by first treating the mixture with about 15 ml $H_2O$ then 30 ml of 30% aqueous NaOH. The reaction mixture was then filtered and the ether layer recovered. The aqueous layer was extracted with ether and the extract combined with the removed ether layer. The ether was distilled away to give 9.2 g of residue. The residue examined by GLC indicated the major products to be about equal amounts of 4-cyclohexenylmethanol,

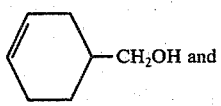 CH₂OH and 4,5-bis(hydroxymethyl)cyclohexene 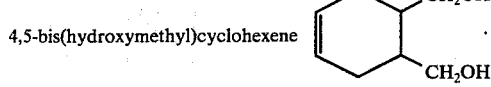

It was estimated that these compounds accounted for 80–90% of the total product. The structures of the above compounds were established by nuclear magnetic resonance (NMR) analyses and mass spectral analyses.

4. Control Run

The occurrence of the 4,5-bis(hydroxymethyl)cyclohexene in the reaction product suggested the possibility that 1,3-butadiene and cis-2-butene-1,4-diol (from polymeric peroxide production and treatment under Oxo conditions) might be the precursors of the cyclic diol through a Diels-Alder reaction. Accordingly, 1,3-butadiene (5 g) and cis-2-butene-1,4-diol (8 g) were reacted in benzene (50 ml) at 121° C under pressure (about 100 psig) for 4 hours. The reactor was cooled, vented and the mixture analyzed by GLC. No evidence of 4,5-bis(hydroxymethyl)cyclohexene was found in the products.

The Oxo reaction of this invention employs a CO pressure generally in the range of from 500 to 2,000 psig and a $H_2$ pressure of from 500 to 2,000 psig.

Reasonable variation and modification are possible within the scope of the foregoing disclosure and the appended claims to the invention the assence of which is that a reaction mass containing a polymeric peroxide as described has been subjected to Oxo reaction conditions following which a reaction mass thus obtained has been subjected to hydrogenation or reducing conditions to produce a carbinol or dicarbinol also as described.

I claim:

1. A process for preparing an unsaturated alicyclic carbinol having the formula

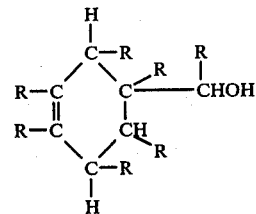

in which each R can be a hydrogen radical or a methyl radical and no more than 3 R's can be methyl radicals; or an unsaturated alicyclic dicarbinol having the formula

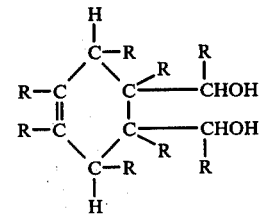

in which each R can be a hydrogen radical or a methyl radical and in which no more than 4 R's can be methyl radicals, or mixtures of said carbinol and said dicarbinol, which process comprises subjecting a polymeric oxidation product having peroxide functionally to an oxo reaction with carbon monoxide, hydrogen, and a metal carbonyl oxo catalyst under reaction conditions sufficient to yield a reaction mixture in which appreciably all of the peroxide functionality has been consumed, and then subjecting said reaction mixture to reducing conditions suitable for reducing carbonylic groups to hydroxyl groups so that no substantial detectable carbonylic groups remain, said reducing conditions further being such that the carbon-carbon double bond in said unsaturated alicyclic carbinol or dicarbinol is preserved, wherein said polymeric oxidation product is produced by the reaction of a conjugated diolefin of the formula

wherein each R is selected from the group consisting of a hydrogen radical and a methyl radical, and at least two of the R substituents of said conjugated diolefin are hydrogen radicals, with oxygen at a temperature in the range of 50° C. to 150° C. under a partial pressure of oxygen of at least 20 pounds per square inch gauge with the total pressure being sufficient to maintain said conjugated diolefin in the liquid phase for a period of time within the range of 0.1 to 25 hours.

2. A process according to claim 1 wherein the oxo reaction involves the treatment of the polymeric oxidation product with carbon monoxide and hydrogen in the presence of a Group VIII metal carbonyl oxo catalyst at a temperature in the range of about 100° to about 200° C.

3. A process according to claim 2 wherein the reduction of the reaction mass that results from the oxo reaction is accomplished by employing hydrogen and a platinum catalyst modified with zinc or ferrous salt or by employing $LiAlH_4$, $NaBH_4$, or $LiBH_4$ as a reducing agent.

4. A process according to claim 3 wherein the Group VIII metal carbonyl oxo catalyst is selected from the group consisting of $Co_2(CO)_8$, $Rh_2(CO)_8$, and $Ir_2(CO)_8$.

5. A process according to claim 3 wherein the carbon monoxide and hydrogen are each employed at pressures in the range of about 500 to about 2,000 psig in the oxo reaction.

6. A process according to claim 5 wherein the amount of metal carbonyl oxo catalyst employed in the oxo reaction is in the range of 1 to 10 parts by weight per 100 parts by weight of the polymeric oxidation product.

7. A process according to claim 6 wherein the conjugated diolefin is 1,3-butadiene.

8. A process according to claim 7 wherein the Group VIII metal carbonyl oxo catalyst is selected from the group consisting of $Co_2(CO)_8$, $Rh_2(CO)_8$, and $Ir_2(CO)_8$.

9. A process according to claim 8 wherein the partial pressure of oxygen in the oxo reaction is no greater than 100 psig.

10. A process according to claim 9 wherein the Group VIII metal carbonyl oxo catalyst is $Co_2(CO)_8$.

11. A process according to claim 10 wherein the reduction of the reaction mass that results from the oxo reaction is accomplished by employing $LiAlH_4$.

12. A process according to claim 11 wherein 4-cyclohexenylmethanol, 4,5-bis(hydroxymethyl)cyclohexene, or mixtures thereof are produced.

13. A process according to claim 3 wherein the reduction is accomplished by hydrogenation using a platinum metal catalyst modified with zinc or ferrous salt.

14. A process according to claim 3 wherein the reduction is accomplished by using a reducing agent selected from the group consisting of $LiAlH_4$, $NaBH_4$, and $LiBH_4$.

15. A process for preparing an unsaturated alicyclic carbinol having the formula

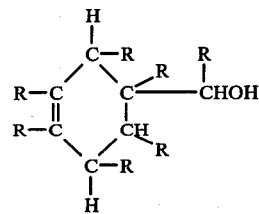

in which each R can be a hydrogen radical or a methyl radical and no more than 3 R's can be methyl radicals, or an unsatruated alicyclic dicarbinol having the formula

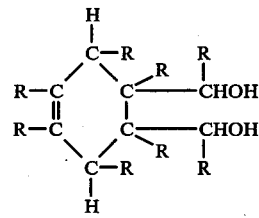

in which each R can be a hydrogen radical or a methyl radical and in which no more than 4 R's can be methyl radicals, which comprises subjecting a polymeric oxidation product of a conjugated diolefin having the formula

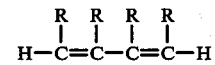

wherein each R is selected from the group consisting of a hydrogen radical and a methyl radical, and at least two of said R substituents are hydrogen radicals, said polymeric oxidation product comprising repeating units of the type $\{R'—O—O\}$ wherein R' is selected from the group consisting of

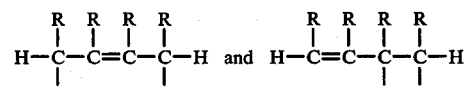

wherein each R is selected from the group consisting of a hydrogen radical and a methyl radical, and at least two of said R substituents are hydrogen radicals, to an oxo reaction with carbon monoxide, hydrogen, and a metal carbonyl oxo catalyst under reaction conditions which will yield a reaction mass in which substantially all of the peroxide functionality has been destroyed, and then subjecting the reaction mass to reducing conditions suitable for converting any carbonyl group in the reaction mass to hydroxyl groups without saturating the unsaturated carbon-carbon linkage in the cyclic ring, said reduction being performed by employing hydrogen and a platinum catalyst modified with zinc or ferrous salt or by employing $LiAlH_4$, $NaBH_4$, or $LiBH_4$ as a reducing agent.

16. A process according to claim 15 wherein the metal carbonyl catalyst is $Co_2(CO)_8$.

17. A process according to claim 15 wherein R' in the polymeric oxidation product is selected from the group consisting of

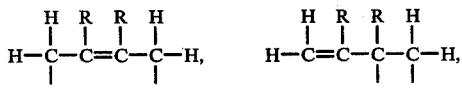

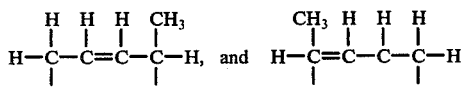

wherein each R is a methyl or hydrogen radical.

18. A process according to claim 15 wherein the oxo reaction is conducted at 100°–200° C and the carbon monoxide and hydrogen are each employed at pressures in the range of about 500 to about 2,000 psig.

19. A process according to claim 18 wherein the reduction is accomplished by hydrogenation using a modified platinum catalyst.

20. A process according to claim 18 wherein the reduction is accomplished by using a reducing agent selected from the group consisting of LiAlH₄, NaBH₄, and LiBH₄.

21. A process according to claim 14 in which the metal carbonyl oxo catalyst is selected from the group consisting of carbonyls of cobalt, rhodium, and iridium.

22. A process for preparing an unsaturated alicyclic carbinol having the formula

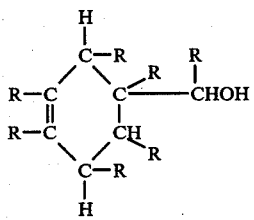

in which each R can be a hydrogen radical or a methyl radical and no more than 3 R's can be methyl radicals, or an unsaturated alicyclic dicarbinol having the formula

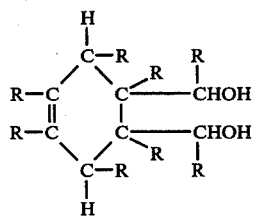

in which each R can be a hydrogen radical or a methyl radical and in which no more than 4 R's can be methyl radicals, which comprises subjecting a polymeric oxidation product of a conjugated diolefin having the formula

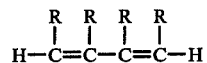

wherein each R is selected from the group consisting of a hydrogen radical and a methyl radical, and at least two of said R substituents are hydrogen radicals, said polymeric oxidation product comprising repeating units of the type ${R'-O-O}$ wherein R' is selected from the group consisting of

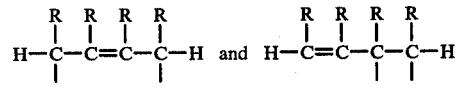

wherein each R is a hydrogen radical or a methyl radical, and at least two of said R substituents are hydrogen radicals, to an oxo reaction with carbon monoxide, hydrogen, and a metal carbonyl oxo catalyst selected from the group consisting of Co₂(CO)₈, Rh₂(CO)₈, and Ir₂(CO)₈, said reaction being conducted at a temperature in the range of about 100° to about 200° C with both the carbon monoxide and hydrogen being employed at pressures in the range of about 500 to about 2,000 psig for a time sufficient to yield a reaction mass in which substantially all of the peroxide functionality has been destroyed, and then subjecting the reaction mass to reducing conditions suitable for converting any carbonyl group in the reaction mass to hydroxyl groups without saturating the unsaturated carbon-carbon linkage in the cyclic ring, said reduction being performed by employing hydrogen and a platinum catalyst modified with zinc or ferrous salt or by employing LiAlH₄, NaBH₄, or LiBH₄ as a reducing agent.

23. A process according to claim 22 wherein R' in the polymeric oxidation product is selected from the group consisting of

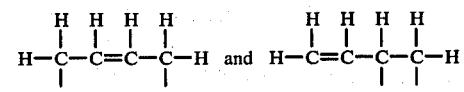

24. A process according to claim 22 wherein the reduction is accomplished using a reducing agent selected from the group consisting of LiAlH₄, NaBH₄, and LiBH₄.

25. A process according to claim 22 wherein the oxo reaction is conducted with the carbon monoxide and hydrogen each being employed at about 1,000 psig.

26. A process according to claim 22 wherein the reduction is accomplished by hydrogenation with platinum metal catalyst modified with zinc or ferrous salts.

27. A process for preparing an unsaturated alicyclic carbinol having the formula

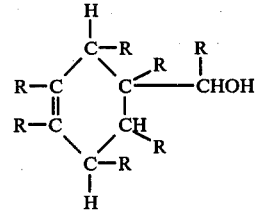

in which each R can be a hydrogen radical or a methyl radical and no more than 3 R's can be methyl radicals, or an unsaturated alicyclic dicarbinol having the formula

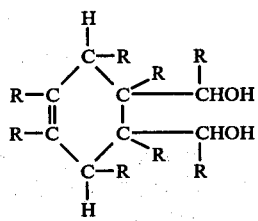

in which each R can be a hydrogen radical or a methyl radical and in which no more than 4 R's can be methyl radicals, which comprises subjecting a polymeric oxidation product of a conjutaged diolefin having the formula

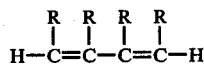

wherein each R is selected from the group consisting of a hydrogen radical and a methyl radical, and at least two of said R substituents are hydrogen radicals, said polymeric oxidation product comprising repeating units of the type $\{R'-O-O\}$ wherein R' is selected from the group consisting of

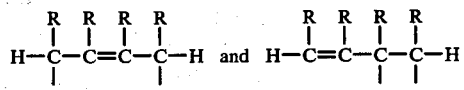

wherein each R is selected from the group consisting of a hydrogen radical and a methyl radical, and at least two of said R substituents are hydrogen radicals, to an oxo reaction with carbon monoxide, hydrogen, and a metal carbonyl oxo catalyst under reaction conditions which will produce a reaction mixture in which the peroxidic material has been appreciably consumed, and then subjecting said reaction mixture to reducing conditions suitable for reducing carbonylic groups present in said reaction mixture to hydroxyl groups so that no substantial detectable carbonylic groups remain, said reduction conditions further being such that carbon-carbon double bond in the product is essentially unaffected.

28. A process according to claim 27 wherein the oxo reaction involves the treatment of the polymeric oxidation product with carbon monoxide and hydrogen in the presence of a Group VIII metal carbonyl oxo catalyst at a temperature in the range of about 100° to about 200° C.

29. A process according to claim 28 wherein the reduction to which the product of the oxo reaction is subjected is accomplished by employing hydrogen and a platinum catalyst modified with zinc or ferrous salt or by employing $LiAlH_4$, $NaBH_4$, or $LiBH_4$ as a reducing agent.

30. A process according to claim 28 wherein the product is at least one of 4-cyclohexene methanol and 4-cyclohexene-1,2-dimethanol and the polymeric oxidation product is produced from 1,3-butadiene.

31. A process according to claim 30 wherein the oxo reaction involves treatment of the polymeric oxidation product with a carbon monoxide and hydrogen in the presence of 1 to 10 parts by weight of Group VIII metal carbonyl oxo catalyst for every 100 parts by weight of polymeric oxidation product.

32. A process for preparing an unsaturated alicyclic carbinol having the formula

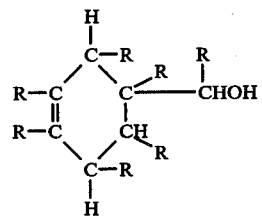

in which each R can be a hydrogen radical or a methyl radical and no more than 3 R's can be methyl radicals, or an unsaturated alicyclic dicarbinol having the formula

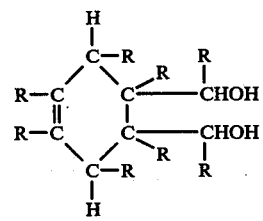

in which each R can be a hydrogen radical or a methyl radical and in which no more than 4 R's can be methyl radicals, which comprises subjecting a polymeric oxidation product of a conjugated diolefin having the formula

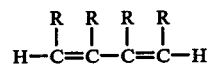

wherein each R is selected from the group consisting of a hydrogen radical and a methyl radical, and at least two of said R substituents are hydrogen radicals, said polymeric oxidation product comprising repeating units of the type $\{R'-O-O\}$ wherein R' is selected from the group consisting of

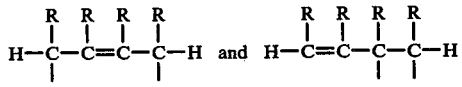

wherein each R is a hydrogen radical or a methyl radical, and at least two of said R substituents are hydrogen radicals, to an oxo reaction with carbon monoxide, hydrogen, and a metal carbonyl Group VIII oxo catalyst under reaction conditions sufficient to yield a reaction mass in which the peroxidic material has been appreciably consumed, and then subjecting the reaction mass to reducing conditions suitable for reducing carbonylic groups to hydroxyl groups so that no substantial detectable carbonylic groups remain while essentially unaffecting carbon-carbon double bonds, said reduction being performed by employing hydrogen and a platinum catalyst modified with zinc or ferrous salt or by employing $LiAlH_4$, $NaBH_4$, or $LiBH_4$ as a reducing agent.

33. A process according to claim 32 wherein the metal carbonyl catalyst is $Co_2(CO)_8$.

34. A process according to claim 32 wherein R' in the polymeric oxidation product is selected from the group consisting of

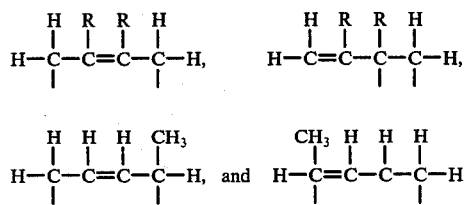

wherein R is methyl or hydrogen.

35. A process according to claim 32 wherein the oxo reaction is conducted at 100°–200° C. and the carbon monoxide and hydrogen are each employed at pressures in the range of about 500 to about 2,000 psig.

36. A process according to claim 35 wherein the reduction is accomplished by hydrogenation using a modified platinum catalyst.

37. A process according to claim 35 wherein the reduction is accomplished by using a reducing agent selected from the group consisting of $LiAlH_4$, $NaBH_4$, and $LiBH_4$.

38. A process according to claim 32 in which the metal carbonyl oxo catalyst is selected from the group consisting of carbonyls of cobalt, rhodium, and iridium.

39. A process for preparing an unsaturated alicyclic carbinol having the formula

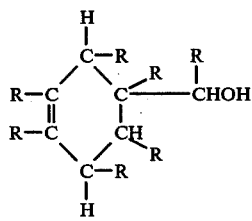

in which each R can be a hydrogen radical or a methyl radical and no more than 3 R's can be methyl radicals, or an unsaturated alicyclic dicarbinol having the formula

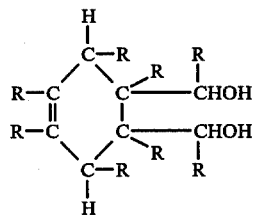

in which each R can be a hydrogen radical or a methyl radical and in which no more than 4 R's can be methyl radicals, which comprises subjecting a polymeric oxidation product of a conjugated diolefin having the formula

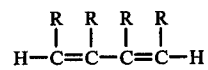

wherein each R is selected from the group consisting of a hydrogen radical and a methyl radical, and at least two of said R substituents are hydrogen radicals, said polymeric oxidation product comprising repeating units of the type ${R'—O—O}$ wherein R' is selected from the group consisting of

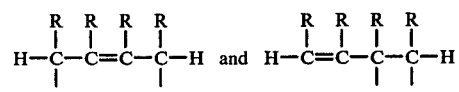

wherein R is hydrogen or methyl, and at least two of said R substituents are hydrogen, to an oxo reaction with carbon monoxide, hydrogen, and a metal carbonyl oxo catalyst selected from the group consisting of $Co_2(CO)_8$, $Rh_2(CO)_8$, and $Ir_2(CO)_8$, said reaction being conducted at a temperature in the range of about 100° to about 200° C. with both the carbon monoxide and hydrogen being employed at pressures in the range of about 500 to about 2,000 psig for a time sufficient to yield a reaction mass in which the peroxidic material has been appreciably consumed, and then subjecting the reaction mass to reducing conditions suitable for converting carbonylic groups to hydroxyl groups so that no substantial detectable carbonylic groups remain while essentially unaffecting carbon-carbon double bonds, said reduction being performed by employing hydrogen and a platinum catalyst modified with zinc or ferrous salt or by employing $LiAlH_4$, $NaBH_4$, or $LiBH_4$ as a reducing agent.

40. A process according to claim 39 wherein R' in the polymeric oxidation product is selected from the group consisting of

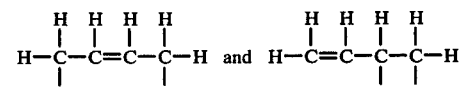

41. A process according to claim 39 wherein the reduction is accomplished using a reducing agent selected from the group consisting of $LiAlH_4$, $NaBH_4$, and $LiBH_4$.

42. A process according to claim 39 wherein the oxo reaction is conducted with the carbon monoxide and hydrogen each being employed at about 1,000 psig.

43. A process according to claim 39 wherein the reduction is accomplished by hydrogenation with platinum metal catalyst modified with zinc or ferrous salts.

* * * * *

UNITED STATES PATENT AND TRADEMARK OFFICE
CERTIFICATE OF CORRECTION

PATENT NO. : 4,038,326
DATED : July 26, 1977
INVENTOR(S) : Donald G. Kuper

It is certified that error appears in the above-identified patent and that said Letters Patent are hereby corrected as shown below:

Column 9, line 23, for "claim 14" read -- claim 15 --.
Column 10, line 28, for "LialH4" read -- LiAlH4 --.

Signed and Sealed this

Eighth Day of August 1978

[SEAL]

Attest:

RUTH C. MASON
Attesting Officer

DONALD W. BANNER
Commissioner of Patents and Trademarks